United States Patent
Kumar et al.

(10) Patent No.: US 12,426,996 B2
(45) Date of Patent: Sep. 30, 2025

(54) DENTAL MEMBRANE

(71) Applicant: BIOMET 3i, LLC, Palm Beach Gardens, FL (US)

(72) Inventors: Kaushal Kumar, Palm Beach Gardens, FL (US); Jay Jayashankar, Warsaw, IN (US)

(73) Assignee: Biomet 3i, LLC, Palm Beach Gardens, FL (US)

( * ) Notice: Subject to any disclaimer, the term of this patent is extended or adjusted under 35 U.S.C. 154(b) by 385 days.

(21) Appl. No.: 18/091,122

(22) Filed: Dec. 29, 2022

(65) Prior Publication Data

US 2023/0210638 A1   Jul. 6, 2023

Related U.S. Application Data

(60) Provisional application No. 63/295,763, filed on Dec. 31, 2021.

(51) Int. Cl.
*A61C 8/00* (2006.01)
*A61C 8/02* (2006.01)

(52) U.S. Cl.
CPC .......... *A61C 8/0006* (2013.01); *A61C 8/0012* (2013.01); *A61C 8/003* (2013.01)

(58) Field of Classification Search
CPC ..... A61C 8/0031; A61C 8/0027; A61C 8/003; A61C 8/0006; A61C 8/0012
USPC ........................................................ 433/173
See application file for complete search history.

(56) References Cited

U.S. PATENT DOCUMENTS

| | | | | |
|---|---|---|---|---|
| 2008/0044449 A1* | 2/2008 | McKay | ............... | A61F 2/30907 424/602 |
| 2010/0268337 A1* | 10/2010 | Gordon | ..................... | A61F 2/28 428/218 |
| 2011/0008754 A1* | 1/2011 | Bassett | ................ | A61C 8/0013 433/175 |
| 2011/0257753 A1* | 10/2011 | Gordon | ..................... | A61F 2/32 623/18.11 |
| 2015/0209472 A1* | 7/2015 | McCoy | ................ | A61C 8/0013 606/301 |
| 2015/0343115 A1* | 12/2015 | Jang | ..................... | A61L 27/3608 623/17.17 |
| 2015/0366641 A1* | 12/2015 | Malinin | ............... | A61C 13/081 433/163 |
| 2017/0151040 A1* | 6/2017 | Wychowanski | ...... | A61C 8/0012 |
| 2017/0202645 A1* | 7/2017 | Malinin | ............... | A61C 8/0039 |
| 2018/0036127 A1* | 2/2018 | Tadic | ................... | A61C 8/0092 |
| 2019/0022273 A1* | 1/2019 | Hess | ..................... | A61B 17/70 |
| 2021/0154015 A1* | 5/2021 | Roshkovan | .......... | A61F 2/2846 |
| 2022/0323786 A1* | 10/2022 | Miller | ................. | A61C 1/0015 |
| 2023/0210638 A1* | 7/2023 | Kumar | ................ | A61C 8/0006 433/173 |
| 2023/0210639 A1* | 7/2023 | Kumar | ................ | A61C 8/0006 433/215 |

(Continued)

*Primary Examiner* — Matthew M Nelson
(74) *Attorney, Agent, or Firm* — Sheridan Ross P.C.

(57) ABSTRACT

A dental membrane that is used with a patient having insufficient bone at a surgical site during a ridge augmentation. The dental membrane includes a first layer and a second layer. The first layer is cortical bone or formed from artificial bone materials to have characteristics of cortical bone. The second layer is cancellous bone or formed from artificial bone materials to have characteristics of cancellous bone.

20 Claims, 5 Drawing Sheets

(56) References Cited

U.S. PATENT DOCUMENTS

2023/0211047 A1\* 7/2023 Kumar ................ A61L 27/3683
424/549

\* cited by examiner

DENTAL MEMBRANE

CROSS-REFERENCE TO RELATED APPLICATIONS

This application claims the benefit of U.S. Provisional Application No. 63/295,763, titled "DENTAL MEMBRANE" and filed on Dec. 31, 2021, which application is incorporated herein by reference in its entirety.

TECHNICAL FIELD

The present disclosure relates to a dental membrane and more specifically to a dental membrane and a method and system for making and using the dental membrane.

BACKGROUND

Dental implants are commonly used as anchoring members in prosthodontics restorations to provide prosthetic teeth at one or more edentulous sites in a patient's dentition at which the patient's original natural teeth have been lost or damaged. Due to tooth decay, periodontal diseases, accidental injury, anatomical abnormalities, bone, gum and/or tooth loss, trauma, tumors, infections and other complications, a natural tooth of a patient may be removed or missing. As a result, dental implant devices may be implanted in the patient's bone structure to improve the patient's physical appearance and/or tooth function.

When an extracted or otherwise missing tooth is not immediately grafted or replaced with an implant, atrophy of the jawbone occurs over time and bone may begin to resorb. Consequently, individuals who have been partially edentulous for an extended period are left with an atrophic alveolar ridge that cannot securely support a dental implant/prosthesis.

In some cases, a ridge augmentation procedure is employed to add bone (e.g., bone height) to the jaw so that sufficient alveolar bone exists to place dental implants. With bone grafting-techniques for ridge augmentation, bone that has been lost may be built up again, therefore benefiting a patient's health and/or appearance by strengthening their jawbone and allowing more effective tooth replacement.

During a bone grafting procedure, a bone graft may be inserted into a socket in the patient's jaw and powder may be poured into any remaining void(s) between the bone graft and the socket. A membrane may then be sutured on top of the void. Conventional membranes may be formed from allograft or xenograft skin. However, a conventional membrane may not maintain its shape and therefore the membrane and the bone graft may deform when experiencing pressure. For example, a divot may form on the bone graft and the membrane when a patient chews food, thereby exerting pressure on the membrane and the bone graft.

Further, in some instances, depending on the bone void shape and location, an additional fixture may be used to contain the bone graft material within the bone void. For example, titanium mesh fixtures have been used to contain bone graft material within a bone void during a bone augmentation. However, the fixture, e.g., a titanium mesh, is a foreign body and can cause various issues and is required to be removed after the bone augmentation. Thus, the fixture requires a patient to undergo a further procedure. The removal of these fixtures can cause tissue disruption that undesirably exposes new bone and disrupts vascularity leading to associated complications or can be difficult to remove due to bone overgrowth.

SUMMARY

The present disclosure provides a dental membrane. The dental membrane can facilitate and promote ingrowth of the surrounding bone into the dental membrane, thereby rebuilding a suitable foundation for affixation of dental implants.

In at least one example, the dental membrane can be formed from bone materials such as allograft or autogenous bone and/or artificial bone material.

In at least one example, the dental membrane includes a first layer formed from or having the properties of cortical bone and a second layer formed from or having the properties of cancellous bone. As discussed herein, the bone void can be filled with a bone graft substitute/material and the dental membrane can cover the bone graft substitute/material placed in the surgical site in order to separate hard tissue from soft tissue. The dental membrane can be sufficiently rigid so as to not deform under chewing or accidental forces, maintain the desired shape of the ridge augmentation, and prevent ingrowth of soft tissue. The dental membrane can assist in the remodeling of the new bone forming from the bone graft material. That is, the second layer can increase the bone growth between the new bone being regenerated and the first layer. Since the dental membrane is formed from bone materials (allograft, autogenous, or artificial), a patient would not need to undergo further procedures to remove foreign bodies.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present disclosure will become apparent to those skilled in the art upon consideration of the embodiment descriptions provided hereinbelow.

These and other examples, advantages, and features of the present dental membranes will be set forth in part in the following Detailed Description and the accompanying drawings. This Overview is intended to provide non-limiting examples of the present subject matter—it is not intended to provide an exclusive or exhaustive explanation. The Detailed Description and drawings are included to provide further information about the present porous metal dental implants.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

Figure 1:
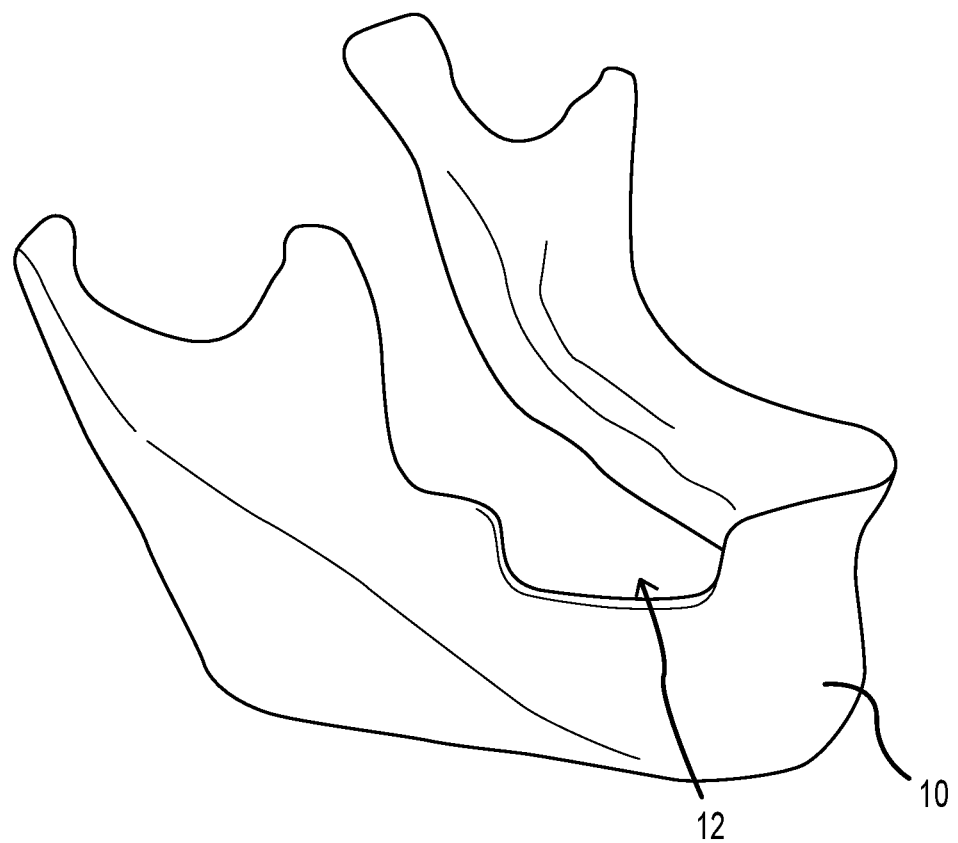
FIG. 1 illustrates a perspective view of a jaw with insufficient bone for implant placement.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The present disclosure provides a dental membrane that can be used during, for example, ridge augmentation. The dental membrane can be porous such that mandibular or maxillary bone can grow into the porous bone material of the dental membrane to provide a stable foundation of support such as for dental implants. The dental membrane, as discussed herein, includes a first layer formed from or having the characteristics of cortical bone and a second layer formed from or having the characteristics of cancellous bone. The dental membrane is able to maintain a shape during remodeling as well as become part of the remodeled ridge. While described with reference to a dental ridge augmentation, the porous membrane can be used in place wherever bone remodeling is needed, e.g., but not limited to, spinal applications, maxillofacial reconstructions, and other orthopedic procedures. For example, the membrane disclosed can be used for guided bone regeneration procedures where the membrane acts as a barrier to prevent soft tissue invasion into the defect and forms a chamber to guide the bone regeneration process.

FIG. 1 shows a patient jaw 10 having insufficient bone at a surgical site 12. The insufficient bone in the patient jaw 10 may be due to factors such as periodontal disease, lost teeth, bone resorption, a thin maxillary and mandibular arch due to genetics, etc. The surgical site 12 can vary between patients and can have a variety of shapes and sizes. During bone regeneration to form a dental ridge sufficient to receive a dental implant, the shape and size of the regenerated bone is important. A bone void surrounded by four walls may be easier to contain bone graft material compared to a bone void only having two or the four walls. As described herein, a dental membrane 14 (see FIG. 2) can be used to contain bone graft material in the bone void as well as provide a rigid support such that chewing forces or accidental forces do not disturb the intended shape of the augmented ridge and maintain separation between the soft and hard tissues. Further, the dental membrane is formed from bone materials or artificial bone such that after the remodeling is complete, the dental membrane becomes part of the dental ridge, thereby reducing additional procedures to the patient.

Figure 2:
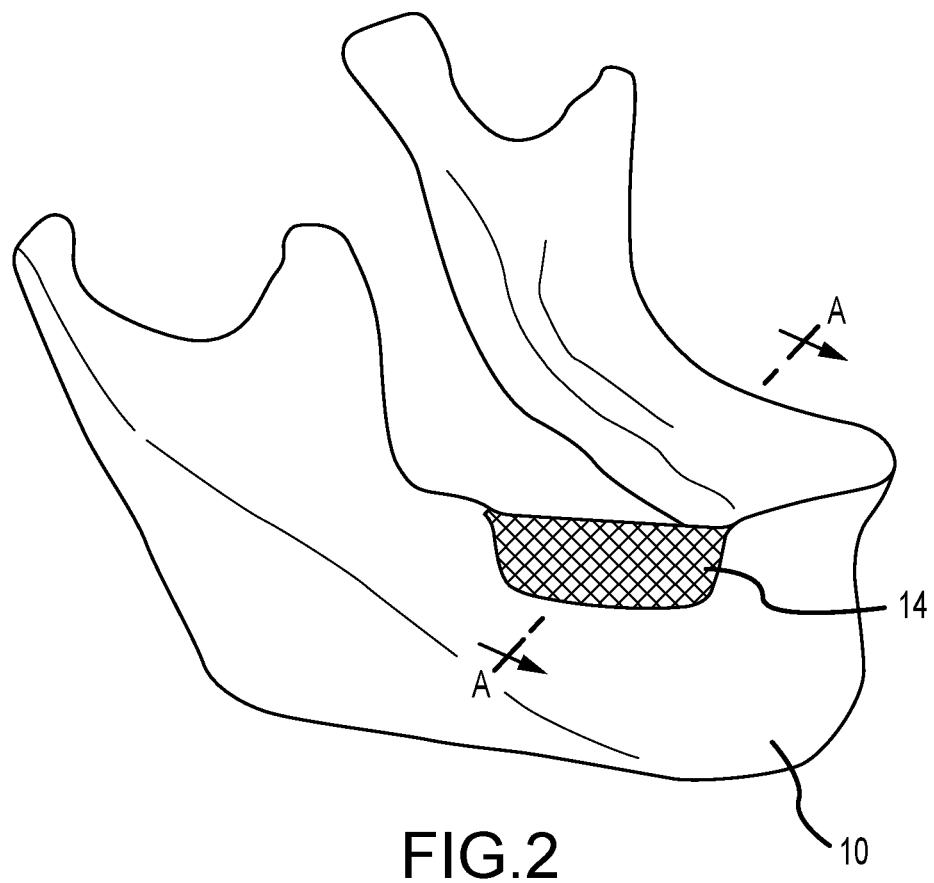
FIG. 2 illustrates a perspective view of the jaw in FIG. 1 with a dental membrane according to at least one embodiment of the present disclosure.
Figure 3:
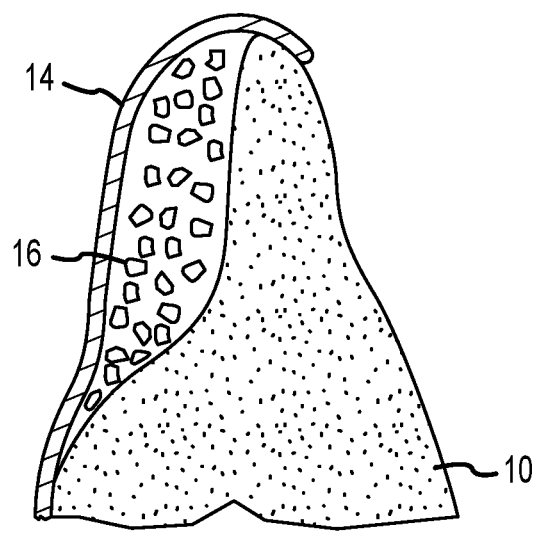
FIG. 3 illustrates a cross-sectional view along A-A of the example shown in FIG. 2 according to at least one embodiment of the present disclosure.

FIG. 2 illustrates a perspective view of the patient's jaw 10 including the dental membrane 14. As shown in FIG. 2, the bone graft material 16 is packed alongside a thin section of the patient's jaw 10. FIG. 3 illustrates a cross-sectional view of the patients jaw 10 in FIG. 2, along line A-A. As discussed herein, the dental membrane 14 can be provided in a variety of shapes and sizes. For example, the dental membrane 14 may be provided in a pre-shaped rectangular arc. During use, the surgeon can modify the shape and/or size of the dental member 14 to conform to the surgical site 12 of the patient.

As seen in FIG. 3, the dental membrane 14 is coupled to the jaw 10 of the patient and the surgical site 12 includes bone graft material 16. In some embodiments, the dental membrane 14 be provided in a malleable so that the surgeon can adjust the dental membrane 14 to create an acceptable ridge. In other embodiments, the dental membrane 14 can be hydrated such that the dental membrane 14 becomes soft or malleable enough to adjust a shape of the dental membrane 14. The dental membrane 14 can be secured to the patient in a variety of ways. For example, the dental membrane 14 can be sutured to the jaw 10 or be used with biocompatible and bioresorbable fasteners to keep the dental membrane 14 in place during healing.

Figure 4:
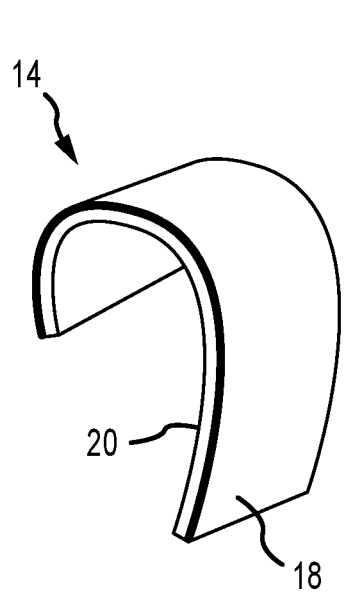
FIG. 4 illustrates a perspective view of an example of a dental membrane according to at least one embodiment of the present disclosure.
Figure 5:
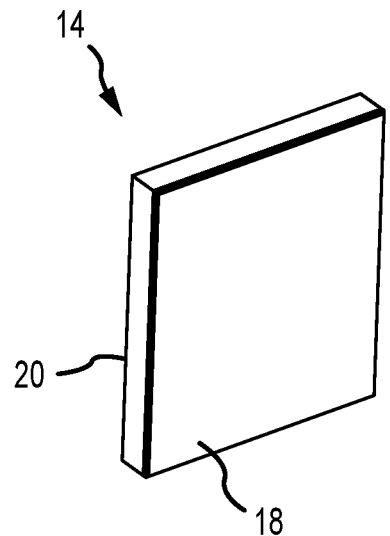
FIG. 5 illustrates a perspective view of an example of a dental membrane according to at least one embodiment of the present disclosure.
Figure 6:
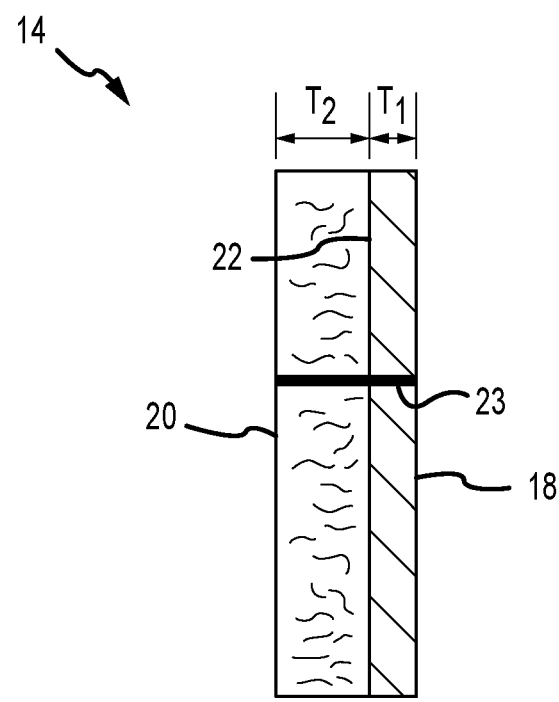
FIG. 6 illustrates a side view of an example of a dental membrane according to at least one embodiment of the present disclosure.

FIG. 4 illustrates a perspective view of an example of a dental membrane 14 having a saddle or arc shape. As shown, the first layer 18 may define an outer surface and the second layer 20 may define an inner surface. In such embodiments, the second layer 20 may face and/or contact the bone graft material 16 at the surgical site 12 and the first layer 20 may face outward from the surgical site 12. FIG. 5 illustrates a perspective view of an example of a dental membrane 15 having a square shape. As discussed herein, the dental membrane 14 can be manufactured having a variety of sizes, shapes, and thicknesses. As seen in FIGS. 4-6, the dental membrane 14 includes a first layer 18 and a second layer 20. It will be appreciated that in some embodiments, the dental membrane 14 may include more than two layers.

In at least one example, the dental membrane 14 can be formed from allograft bone or xenograft bone such that the first layer 18 is cortical bone and the second layer 20 is cancellous bone. The bone (cortical and cancellous) can be obtained from human autologous bone and/or allograft tissue. Autologous and/or allograft tissues are not only biocompatible, but they are strong, and biointegrate in time with the recipient patient's tissue and can be shaped in a desired shape commercially in a manufacturing environment. The bone can also be provided in a sterile form. The dental membrane 14 can be harvested in a desired size and shape or can be formed by combining the first layer 18 and the second layer 20. For example, a cortical bone graft can be coupled to a cancellous bone graft by a biocompatible adhesive 22. In another example, optionally or in combination with the adhesive, a suture 23 (shown in FIG. 6) could be used to combine the first layer 18 and the second layer 20. It will be appreciated that the first layer 18 and the second layer 20 can be combined in any way such as, for example, suturing, adhesion, fasteners, and/or any combination thereof. In other embodiments, the first layer 18 and the second layer 20 may be formed integrally with each other.

As shown in FIG. 6, the first layer 18 may comprise a first thickness T1 and the second layer may comprise a second thickness T2. In some embodiments the first thickness T1 is less than the second thickness T2. In other embodiments, the second thickness T2 is less than the first thickness T1. In still other embodiments, the first thickness T1 and the second thickness T2 are substantially the same. Alternatively or additionally, the first thickness T1 and/or the second thickness T2 may vary in thickness from a first end to a second end of the dental membrane 14.

Typically, the microstructure of cortical bone contains bundles, or fibers, of mineralized collagen that are oriented parallel to the long axis of the bone. Known methods for making demineralized bone particles involve subdividing sections of whole, i.e., mineralized, bone, e.g., by such mechanical operations as shredding, milling, shaving, machining, etc., to provide particles which are then demineralized, e.g., by treatment with acid. The resulting demineralized bone particles exhibit osteoinductive and osteoconductive properties that make them useful as, or in, implants intended for use in oral procedures such as bone enhancement in oral mandible and maxilla procedures, such as for example, alveolar ridge augmentation. In some embodiments, the first layer could provide minimal surface demineralization so that the structural capacity of the cortical layer is not compromised.

It will be understood by those of ordinary skill in the art that in other embodiments the bone material may be obtained from non-human sources (e.g., bovine, ovine, porcine, or the like), such as for example, xenograft material from animal-derived bone tissue.

In some embodiments, the dental membrane 14 can be harvested from bone. The bone can be reconstituted, milled, and/or demineralized in some embodiments. In other embodiments, the dental membrane 14 can also be formed from artificial bone material. That is, the artificial bone material can be fabricated to have similar characteristics as cortical and cancellous bone. In an example, the first layer 18 can be formed to have a similar density and porosity as cortical bone. In some embodiments, the second layer 20 can be formed to have a similar density and porosity as cancellous bone. Thus, artificial bone materials can be used to replicate cortical and cancellous bone. In other embodiments, the first layer 18 replicating cortical bone can have a porosity within about 5 percent (%) to about 10%, with 10 microns (μm) to 50 μm diameter pores. In at least one example, the second layer 18 replicating cancellous bone can have a porosity within about 75% to about 85%, with 300 μm to 600 μm diameter pores. However, other porosities and pore sizes can be used. Generally, since the first layer 18 is for strength, the porosity and pore size of the first layer 18 is less than the porosity and pore size of the second layer 20. Though it will be appreciated that in other embodiments the first layer 18 may have a porosity and pore sizes greater than a porosity and pore sizes of the second layer 20.

Creating the first layer 18 and/or the second layer 20 from artificial bone material may enable customization of the thickness, shape, size, porosity, and pore size among other characteristics of the first layer 18 and/or the second layer 20. As discussed herein, the first layer 18 and the second layer 20 can be coupled with, but not limited to, adhesives, sutures, other fastening mechanisms, and combinations thereof.

In at least one embodiment, one of the first layer 18 or the second layer 20 can be formed from either allograft bone or xenograft bone and the other layer can be formed from the artificial bone material.

In some embodiments, the dental membrane 14 can be mixed, sprayed and/or coated with one or more therapeutic agents to provide an effective amount of the therapeutic agent. Therapeutic agents include, but are not limited to, analgesics, anti-inflammatory agents, anti-infective agents, antibiotics, bisphosphonates or other anti-resorptive agents (e.g. calcitonin), and/or growth factors.

Figure 7:
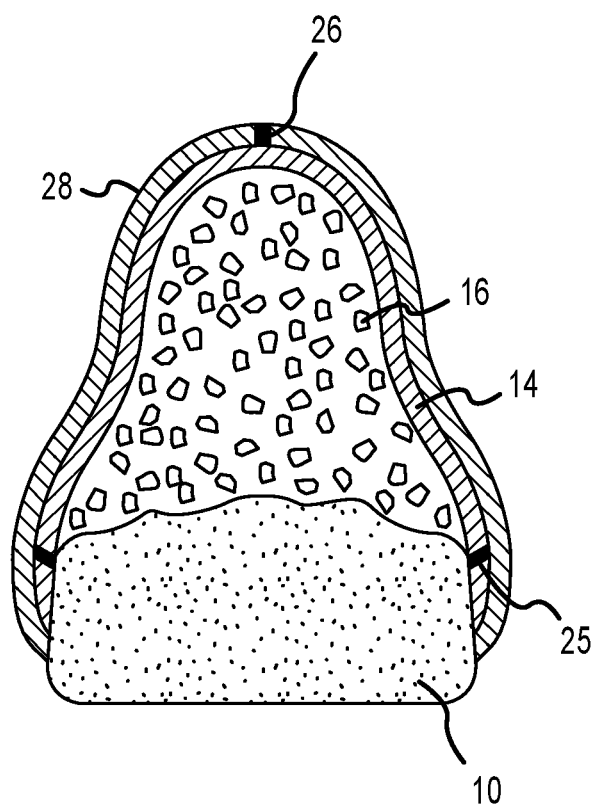
FIG. 7 illustrates a cross-sectional view of an example of a dental membrane according to at least one embodiment of the present disclosure.

FIG. 7 illustrates the use of the dental membrane 14 to create an entire ridge on the jaw 10 of the patient. That is, the dental membrane 14 is forming a lingual side, a buccal side, and a top portion of the ridge. It will be appreciated that during use, one or more dental membranes 14 may be used to cover the bone graft material 16 and the void. Once the bone graft material 16 is packed within the surgical site and covered with the dental membrane 14, the dental membrane 14 can be secured to the jaw 10. As previously described, the dental membrane 14 comprises the first layer 18 and the second layer 20. The first layer 18 may define an outer surface and face outward from the bone graft material 16 and the second layer 20 may define an inner surface and may face and/or contact the bone graft material 16. In such embodiments the first layer 18 may be formed from cortical bone or a material with characteristics of cortical bone and the second layer 20 may be formed from cancellous bone or material with characteristics of cancellous bone. In such embodiments, the cortical bone advantageously acts as a space saving barrier and may prevent soft tissue from growing in the void and the cancellous bone acts as an interface with the bone graft material 16. Further, the cortical bone or the first layer 18 provides thickness and strength in the dental membrane 14 whereas the cancellous layer or the second layer 20 provides flexibility in the dental membrane 14.

As seen in FIG. 7, the dental membrane 14 can be secured to the jaw 10 via sutures 25, but other fastening mechanisms are contemplated. In some embodiments, the gum tissue 28 can be secured over the dental membrane 14, e.g., by use of another suture 26.

Figure 8:
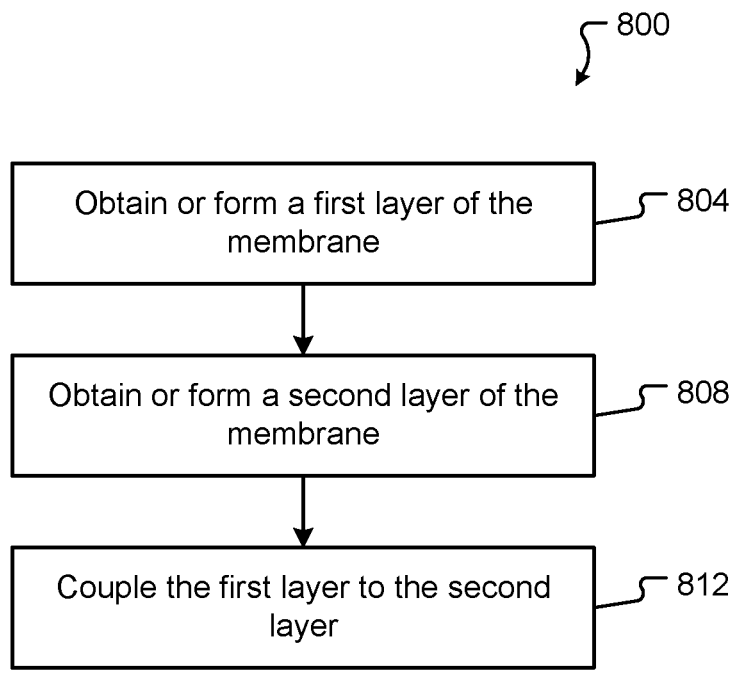
FIG. 8 is a flow diagram for forming a dental membrane according to at least one embodiment of the present disclosure.

FIG. 8 illustrates a flow diagram for forming a dental membrane 14. The dental membrane 14 can be formed by, for example, a manufacturer, a clinician, etc. At step 804, a first layer such as the first layer 18 of cortical bone can be harvested/obtained or a first layer having the characteristics of cortical bone can be formed from artificial bone material, as described herein. At step 808, a second layer such as the second layer 20 of cancellous bone can be harvested/obtained or a second layer having the characteristics of cancellous bone can be formed from artificial bone material, as described herein. At step 812, the first and second layer can be coupled together. For example, a biocompatible adhesive can be used, one or more sutures can be used, the layers can be, e.g., fused together, among other fastening means. The first layer and the second layer can be formed in any shape such as, for example, a rectangle, a square, a triangle, and/or an arc.

Figure 9:
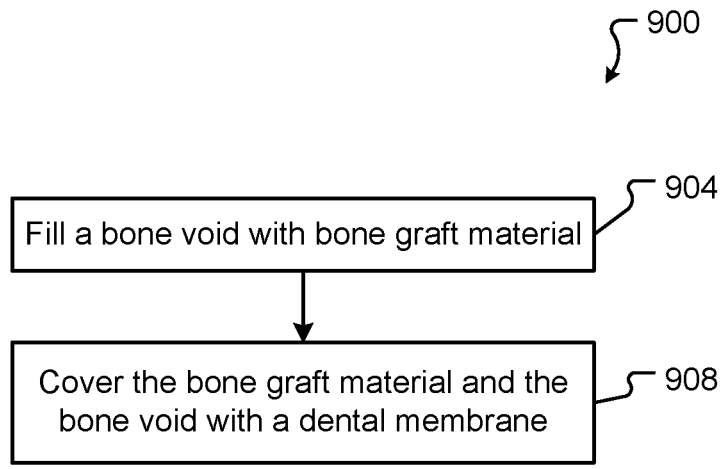
FIG. 9 is an illustrative method of using the dental membrane for a ridge augmentation according to at least one embodiment of the present disclosure.

FIG. 9 illustrates a flow diagram for using the dental membrane 14 for a ridge augmentation. A step 904, the bone void at a surgical site such as the surgical site 12 can be filled with bone graft material/substitute such as the bone graft material 16. At step 908, the bone graft material and bone void are covered with the dental membrane 14, which may be formed using, for example, the method 800 described above. In one example, the dental membrane 14 can be fastened to the jaw of the patient. Additionally, after the dental membrane 14 covers the bone graft material, the surgical site can be sutured closed.

It will be appreciated that the methods 800 and 900 may have fewer or more steps than described above.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

EXAMPLES

To illustrate the dental membrane, a non-limiting list of examples is provided here:

In Example 1, a dental membrane, comprising: a first layer being formed from one of cortical bone and an artificial bone material that has characteristics of cortical bone; and a second layer being formed from one of cancellous bone and an artificial bone material that has characteristics of cancellous bone.

Example 2 can include, or can optionally be combined with the subject matter of Example 1, to optionally include wherein, when the first layer is cortical bone and the second layer is cancellous bone, the first layer and second layer are formed from allograft bone or xenograft bone.

Example 3 can include, or can optionally be combined with the subject matter of one or any combination of Examples 1 or 2 to optionally include wherein, when the first layer and second layer are formed from artificial bone material.

Example 4 can include, or can optionally be combined with the subject matter of one or any combination of Examples 1 through 3 to optionally include wherein the first layer has characteristics of cortical bone.

Example 5 can include, or can optionally be combined with the subject matter of one or any combination of Examples 1 through 4 to optionally include wherein the first layer has a porosity of about 5 percent (%) to about 10%.

Example 6 can include, or can optionally be combined with the subject matter of one or any combination of Examples 1 through 5 to optionally include wherein the first layer has a pore diameter of about 10 microns (μm) to about 50 μm.

Example 7 can include, or can optionally be combined with the subject matter of one or any combination of Examples 1 through 6 to optionally include wherein the second layer has characteristics of cancellous bone.

Example 8 can include, or can optionally be combined with the subject matter of one or any combination of Examples 1 through 7 to optionally include wherein the first layer has a porosity of about 75% to about 85%.

Example 9 can include, or can optionally be combined with the subject matter of one or any combination of Examples 1 through 8 to optionally include wherein the first layer has a pore diameter of about 300 μm to about 600 μm.

Example 10 can include, or can optionally be combined with the subject matter of one or any combination of Examples 1 through 9 to optionally include wherein the first layer and the second layer are formed integrally with each other.

Example 11 can include, or can optionally be combined with the subject matter of one or any combination of Examples 1 through 10 to optionally include wherein first layer and the second layer are coupled together.

Example 12 can include, or can optionally be combined with the subject matter of one or any combination of Examples 1 through 11 to optionally include where in the first layer and the second layer are coupled together with at least one of a biocompatible adhesive and one or more sutures.

Example 13 can include, or can optionally be combined with the subject matter of one or any combination of Examples 1 through 12 to optionally include wherein a porosity of the first layer is less than a porosity of the second layer.

Example 14 can include, or can optionally be combined with the subject matter of one or any combination of Examples 1 through 13 to optionally include wherein a thickness of the first layer is less than a thickness of the second layer.

Example 15 can include, or can optionally be combined with the subject matter of one or any combination of Examples 1 through 14 to optionally include wherein a thickness of the first layer is greater than a thickness of the second layer.

Example 16 can include, or can optionally be combined with the subject matter of one or any combination of Examples 1 through 15 to optionally include wherein a thickness of the first layer is equal to a thickness of the second layer.

Example 17, a method of forming a dental membrane, the method comprising: obtaining a first layer of cortical bone; obtaining a second layer of cancellous bone; and coupling the first layer to the second layer.

Example 18 can include, or can optionally be combined with the subject matter of Example 17, to optionally include wherein at least one of the first layer and the second layer are one of an allograft an xenograft.

Example 19 can include, or can optionally be combined with the subject matter of one or any combination of Examples 17 or 18 to optionally include wherein at least one of the first layer and the second layer are formed from an artificial bone material.

In Example 20, a method of using a dental membrane, the method including: forming or obtaining the dental membrane including a first layer and a second layer, wherein the first layer has a porosity that is less than a porosity of the second layer; packing a surgical site of a patient with bone graft substitute; and covering the surgical site including the bone graft substitute with the dental membrane.

Example 21 can include, or can optionally be combined with the subject matter of Example 20, to optionally include wherein, after a healing period, installing a dental implant at the surgical site, wherein the dental membrane has become integral with surrounding bone at the surgical site.

Example 22 can include, or can optionally be combined with the subject matter of one or any combination of Examples 20 or 21 to optionally include wherein the dental membrane is not removed from the patient.

Example 23, a dental membrane, comprising: a first layer being formed from cortical bone; and a second layer being formed from cancellous bone, wherein the first layer is coupled to the second layer with a biocompatible adhesive, wherein the first layer and the second layer form an arc and the first layer defines an outer surface of the arc and the second layer defines an inner surface of the arc, and wherein the first layer has a thickness and a porosity less than a thickness and a porosity of the second layer.

Each of these non-limiting examples can stand on its own, or can be combined in various permutations or combinations with one or more of the other examples

What is claimed is:

1. A dental membrane, comprising:
   a first layer having a first composition, the first composition comprising one or more of cortical bone and an artificial bone material that has characteristics of cortical bone; and
   a second layer having a second composition, the second composition comprising one or more of cancellous bone and an artificial bone material that has characteristics of cancellous bone, wherein the first layer is coupled to the second layer, wherein the first composition is different from the second composition, and wherein a first porosity of the first layer is less than a second porosity of the second layer and/or a first age pore diameter of the first layer is smaller than a second average pore diameter of the second layer.

2. The dental membrane of claim 1, wherein when the first layer is predominantly cortical bone and the second layer is predominantly cancellous bone, the first layer and second layer are formed from allograft bone or xenograft bone.

3. The dental membrane of claim 1, wherein the first layer and second layer are formed from artificial bone material.

4. The dental membrane of claim 3, wherein the first layer has a porosity of about 5 percent (%) to about 10%.

5. The dental membrane of claim 3, wherein the first layer has a pore diameter of about 10 microns (μm) to about 50 μm.

6. The dental membrane of claim 3, wherein the second layer has characteristics of cancellous bone.

7. The dental membrane of claim 6, wherein the first layer has a porosity of about 75% to about 85%.

8. The dental membrane of claim 6, wherein the first layer has a pore diameter of about 300 μm to about 600 μm.

9. The dental membrane of claim 1, wherein the first layer and the second layer are formed integrally with each other.

10. The dental membrane of claim 1, wherein first layer and the second layer are coupled together.

11. The dental membrane of claim 10, wherein the first layer and the second layer are coupled together with at least one of a biocompatible adhesive and one or more sutures.

12. The dental membrane of claim 1, wherein a porosity of the first layer is less than a porosity of the second layer.

13. The dental membrane of claim 1, wherein a thickness of the first layer is less than a thickness of the second layer.

14. The dental membrane of claim 1, wherein a thickness of the first layer is greater than a thickness of the second layer.

15. The dental membrane of claim 1, wherein a thickness of the first layer is equal to a thickness of the second layer.

16. A method of forming a dental membrane, the method comprising:
    obtaining a first layer comprising predominantly cortical bone;
    obtaining a second layer comprising predominantly cancellous bone; and
    coupling the first layer to the second layer, wherein a first composition of the first layer is different than a second composition of the second layer, wherein a first porosity of the first layer is less than a second porosity of the second layer, and wherein an average pore size of the first layer is less than an average pore size of the second layer.

17. The method of claim 16, wherein at least one of the first layer and the second layer are one of an allograft an xenograft.

18. The method of claim 16, wherein the dental membrane is shaped in a rectangular arc.

19. The method of claim 16, wherein a thickness of the first layer is less than a thickness of the second layer.

20. A dental membrane, comprising:
    a first layer being formed from cortical bone; and
    a second layer being formed from cancellous bone, the first and second layers having different compositions,
    wherein the first layer is coupled to the second layer with a biocompatible adhesive, wherein the first layer and the second layer form an arc and the first layer defines an outer surface of the arc and the second layer defines an inner surface of the arc, and wherein the first layer has a thickness and a porosity less than a thickness and a porosity of the second layer.

* * * * *